United States Patent
Müller et al.

(10) Patent No.: US 6,335,005 B1
(45) Date of Patent: *Jan. 1, 2002

(54) AQUEOUS COSMETIC COMPOUNDS

(75) Inventors: Wolfgang Müller, Frankenthal; Bernhard Schlarb, Ludwigshafen; Harm Wiese, Heidelberg; Ellen Pfrommer, Hassloch, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/446,107

(22) PCT Filed: Jun. 18, 1998

(86) PCT No.: PCT/EP98/03733

§ 371 Date: Dec. 23, 1999

§ 102(e) Date: Dec. 23, 1999

(87) PCT Pub. No.: WO99/00104

PCT Pub. Date: Jan. 7, 1999

(30) Foreign Application Priority Data

Jun. 27, 1997 (DE) .......................................... 197 27 504

(51) Int. Cl.$^7$ .......................... A61K 31/74; A61K 7/00; A61K 9/00; A61K 7/06; C08F 2/22
(52) U.S. Cl. .................... 424/78.02; 424/401; 424/400; 424/70.1; 524/460
(58) Field of Search ................................. 424/401, 400, 424/70.1, 78.02; 524/460; 526/323.2

(56) References Cited

U.S. PATENT DOCUMENTS 5,889,101 A * 3/1999 Schlarb et al. ............... 524/460

FOREIGN PATENT DOCUMENTS

| EP | 0 424 112 | 4/1991 |
| EP | 0 727 441 | 8/1996 |
| EP | 0 815 848 | 1/1998 |

OTHER PUBLICATIONS

Schlarb et al., "Hydroresin Dispersion", Progress in Organic Coatings, vol. 29, No. 1–4, pp. 201–208.*
English Translation Of International Preliminary Examination Report submitted by applicants for which there was no form 1449.*
Bernhard Schlarb, et al., "Hydroresin Dispersions", Progress in Organic Coatings, vol. 29, No. 1–4, pp. 1 201–208, XP002095008.

* cited by examiner

Primary Examiner—Thurman K. Page
Assistant Examiner—Blessing Fubara
(74) Attorney, Agent, or Firm—Oblon, Spivak, McClelland, Maier & Neustadt, P.C.

(57) ABSTRACT

The use of an emulsion polymer in aqueous cosmetic compositions, wherein the emulsion polymer is obtainable by emulsion polymerization of a monomer mixture A comprising from 50 to 100% by weight, based on the monomer mixture, of $C_1$–$C_{18}$ alkyl (meth)acrylates, vinyl esters, vinylaromatic compounds or mixtures thereof in the presence of a polymer B which has been built up from $b_1$) from 5 to 50% by weight of monomers having at least one ionic group or one group which can be converted into an ionic group, $b_2$) from 0 to 95% by weight of $C_1$–$C_{18}$ alkyl (meth)acrylates, vinyl esters, vinylaromatic compounds or mixtures thereof, and $b_3$) from 0 to 50% by weight of further monomers, the glass transition temperature of the polymer built up from monomer mixture A being less than or equal to that of the polymer B.

29 Claims, No Drawings

AQUEOUS COSMETIC COMPOUNDS

The invention relates to the use of an emulsion polymer in aqueous cosmetic compositions, wherein the emulsion polymer is obtainable by emulsion polymerization of a monomer mixture A comprising from 50 to 100% by weight, based on the monomer mixture, of $C_1$–$C_{18}$ alkyl (meth) acrylates, vinyl esters, vinylaromatic compounds or mixtures thereof in the presence of a Polymer B which has been built up from $b_1$) from 5 to 50% by weight of monomers having at least one ionic group or one group which can be converted into an ionic group, $b_2$) from 0 to 95% by weight of $C_1$–$C_{18}$ alkyl (meth) acrylates, vinyl esters, vinylaromatic compounds or mixtures thereof, and $b_3$) from 0 to 50% by weight of further monomers, the glass transition temperature of the polymer built up from monomer mixture A being less than or equal to that of the polymer B.

Aqueous cosmetic compositions, including nail varnish compositions, are already known from EP-A-424 122. As binders, the compositions described therein comprise an emulsion polymer with a core/shell structure, where the glass transition temperature of the (hydrophilic) shell is at least 10° C. lower than that of the core. The nail varnish compositions described show a still inadequate adhesion to keratin-containing substrates, in other words to fingernails.

EP-A-727 441 (O.Z. 0050/45626) discloses emulsion polymers which are obtainable by polymerization in the presence of a polymeric protective colloid.

It is an object of the present invention to provide aqueous cosmetic compositions which have good adhesion to keratin-containing substrates and produce films with good water resistance, good gloss, sufficient hardness and high transparency.

We have found that this object is achieved by the use defined at the outset.

As used below, the term monomer represents free-radically copolymerizable compounds having at least one ethylenically unsaturated group.

The emulsion polymer is preferably prepared by emulsion polymerization of the monomer mixture A) in the presence of a polymer B).

The polymer B) consists preferably of from 10 to 30% by weight of monomers $b_1$), from 60 to 90% by weight of monomers $b_2$) and from 0 to 30% by weight of monomers $b_3$).

The percentages by weight are based in each case on the polymer B).

Suitable monomers $b_1$) can be acidic or anionic, basic or cationic, or amphoteric monomers.

It is also possible for anionic and cationic monomers to be present simultaneously in polymer B), with one of the two types of monomer being in excess, from a molar standpoint, so that the dispersion prepared therewith is anionic or cationic. This can be sensible, for example, when one of the two types of monomer brings about an additional advantage, such as improved adhesion or dispersion stability.

Examples of anionic or acidic monomers are polymerizable carboxylic acid derivatives, such as: (meth)acrylic acid, maleic acid and its anhydrides and monoesters, fumaric acid and its monoesters, itaconic acid;

unsaturated sulfonic acid derivatives, such as: styrenesulfonic acid, vinylsulfonic acid, 2-acrylamido-2-methylpropanesulfonic acid or salts thereof;

unsaturated phosphoric or phosphonic acid derivatives, such as: vinylphosphonic acid or the monophosphates of polymerizable alcohols such as butanediol monoacrylate or hydroxyethyl methacrylate.

Examples of cationic or basic monomers are (meth) acrylic esters or (meth)acrylamides of amino alcohols, such as dialkylaminoalkyl (meth)acrylates or dialkylaminoalkyl (meth)acrylamides, for instance N,N-dimethylaminoethyl (meth)acrylates, N,N-diethylaminoethyl methacrylate, N,N-dimethylaminopropylacrylamide, dialkylaminostyrenes, for example N,N-dimethylaminostyrene and N,N-dimethylaminomethylstyrene, vinylpyridines, such as 4-vinylpyridine and 2-vinylpyridine, and also compounds which can be prepared by quaternization of the abovementioned basic monomers using known quaternizing reagents such as alkyl halides, benzyl halides, dialkyl sulfates, etc.

Examples of amphoteric monomers are N-(3-sulfopropyl)-N-methacryloyloxyethyl-N,N-dimethylammonium betaine and N-carboxymethyl-N-methacryloyloxyethyl-N,N-dimethylammonium betaine.

Acid groups or tertiary amino groups can be converted into ionic groups by forming salts or by quaternization.

Examples of monomers $b_2$) (principal monomers) are $C_1$–$C_9$-alkyl, especially $C_1$–$C_8$-alkyl (meth)acrylates, such as methyl methacrylate, methyl acrylate, n-butyl acrylate, ethyl acrylate, 2-ethylhexyl acrylate and n-butyl methacrylate.

Lauryl or stearyl (meth)acrylates can also be mentioned.

Also suitable in particular are mixtures of alkyl (meth) acrylates.

Vinyl esters of carboxylic acids having 1 to 20 C atoms are, for example, vinyl laurate, vinyl stearate, vinyl propionate and vinyl acetate.

Suitable vinylaromatic compounds are vinyltoluene, α- and p-methylstyrene, α-butylstyrene, 4-n-butylstyrene, 4-n-decylstyrene and, preferably, styrene.

The monomers $b_2$) are also preferably employed in a mixture.

Vinylaromatic compounds such as styrene are frequently employed, for example, in a mixture with $C_1$–$C_{18}$-alkyl (meth)acrylates, especially with $C_1$–$C_{18}$-alkyl (meth) acrylates.

Examples of further ethylenically unsaturated monomers $b_3$) are hydroxyl-containing monomers such as hydroxyalkyl (meth)acrylates, for example hydroxypropyl or hydroxyethyl (meth)acrylate, amides or substituted amides of ethylenically unsaturated mono- or dicarboxylic acids, for example acrylamide, methacrylamide, N-methylolacrylamide, N-methylolmethacrylamide, and the N-methylolacrylamides and N-methylolmethacrylamides which are etherified with $C_1$–$C_6$ monohydric alcohols. Crosslinking monomers, for example with two vinyl groups, although they can also be used, are preferably absent from the polymer B or, if present, then only in small amounts, for example below 0.2% by weight, based on the polymer B.

Also deserving of mention are nitriles, vinyl halides and nonaromatic hydrocarbons.

Examples of nitriles are acrylonitrile and methacrylonitrile.

The vinyl halides are ethylenically unsaturated compounds substituted by chlorine, fluorine or bromine, preferably vinyl chloride and vinylidene chloride.

Nonaromatic hydrocarbons having 2 to 8 C atoms and one or two olefinic double bonds which may be mentioned are butadiene, isoprene and chloroprene, and also ethylene, propylene and isobutylene. Nonaromatic hydrocarbons having two double bonds are less preferred principal monomers for preparing the protective colloid.

The weight-average molecular weight ($M_w$) of the polymer B) is preferably more than 10,000, particularly preferably more than 20,000 to 200,000 and, with very particular preference, from 40,000 to 120,000 (determined by gel permeation chromatography using polystyrene as standard and tetrahydrofuran as eluent).

The polymer B) can be prepared, for example, by bulk polymerization, in other words without solvent, or—preferably—by solution polymerization.

The polymers B) prepared by bulk or solution polymerization are preferred, since the polymers are more uniform in structure and include an incorporated hydrophobic (oil-soluble) initiator.

Examples of suitable solvents are those having a boiling point of below 100° C. at 1 bar or those which with water form an azeotrope which can easily be distilled off from the aqueous polymer dispersion if desired. Advantageously, it is also possible to use film-forming aids, such as butylglycol, butyldiglycol or butoxypropanol, as solvents. In this way, subsequent addition of these auxiliaries becomes unnecessary.

Examples which may be given of solvents are butanol, isobutanol, propanol, ethanol, methanol and methyl ethyl ketone.

The ethylenically unsaturated monomers can be polymerized, for example, in a known manner by means of anionic or preferably free-radical polymerization, preferably in the presence of initiators. Examples of free-radical initiators are azobiscarboxamides, azobiscarbonitriles, peracid esters or peroxides. The amount of initiator is preferably from 0.2 to 5, particularly preferably from 0.5 to 3% by weight, based on the monomers. The polymerization temperature is preferably from 50 to 150° C., particularly preferably from 80 to 130° C. It is also possible if desired to add regulators, examples being mercaptoethanol, tert-dodecyl mercaptan or diisopropylxanthogen sulfide, preferably in amounts of from 0 to 3% by weight, based on the monomers.

The polymer B) can be prepared, for example, in one or more stages. In particular it is possible, for example, first to prepare a polymer having a high acid content and then, in the presence of said polymer, to prepare a polymer having a lower acid content (or acid number=0), as is described, for example, in EP-A 320 865.

In the case of the present invention, however, a multistage preparation of this kind is not necessary, and so the single-stage preparation is preferred. For the polymerization the monomers can be introduced as an initial charge or else (preferably) can be metered in continuously.

The polymer B) is obtained as a dispersion or, preferably, solution in the organic solvent. The solids content is preferably from 50 to 95, especially from 60 to 85% by weight.

The polymer B) is then used as a protective colloid in the emulsion polymerization.

For this purpose the polymer B) can be introduced as an initial charge in water and/or can be added to the water in the course of emulsion polymerization together with the monomers to be polymerized.

The polymer B) can be used in the form of its organic solution, for example in the case of solution polymerization, or else in solvent-free form, for example in the case of bulk polymerization. Alternatively, it is possible first to convert it into an aqueous dispersion or solution, and if desired to remove solvent by distillation.

Before or during conversion to the aqueous phase, some or all of the acid groups or anhydride groups of the polymeric protective colloid are converted into salt groups; in other words they are neutralized.

Suitable neutralizing agents are, firstly, mineral bases such as sodium carbonate or potassium carbonate and also ammonia, and secondly organic bases, for example amino alcohols, especially 2-amino-2-methyl-l-propanol (AMP), triethanolamine, triisopropanolamine (TIPA), monoethanolamine, diethanolamine, tri[(2-hydroxy)-1-propyl]amine, 2-amino-2-methyl-1,3-propanediol (AMPD) or 2-amino-2-hydroxymethyl-1,3-propanediol, and also diamines such as lysine.

Insofar as the polymer B) is not already present in an aqueous phase and, accordingly, the conversion to salt groups has already taken place, conversion to salt groups is carried out before or during the addition of the polymer B) to the polymerization batch of the emulsion polymerization.

The proportion by weight of the polymer B) is preferably from 2 to 40 parts by weight, particularly preferably from 5 to 25 parts by weight, based on 100 parts by weight of the polymer obtained by emulsion polymerization (in other words the sum of polymer B and monomer mixture A).

In the emulsion polymerization, no further emulsifiers, protective colloids or other dispersing auxiliaries are required, and therefore are preferably not employed.

The monomers of the monomer mixture A) that are to be polymerized essentially comprise the monomers $b_1$) to $b_3$) already mentioned above, with suitable monomers $b_2$ also including aliphatic hydrocarbons having 2 to 8 C atoms and two double bonds, and suitable monomers $b_3$) also including crosslinking monomers, such as butanediol acrylate and divinylbenzene.

The monomer mixture A) consists preferably to the extent of from 0 to 100, particularly preferably to the extent of from 40 to 100% by weight, of the monomers $b_2$) (principal monomers).

Monomers $b_1$) can but need not necessarily be used; if they are, their proportion, however, is generally in each case below 10% by weight, preferably below 5% by weight, and, with particular preference, below 3% by weight.

Further monomers $b_3$) can likewise be used, for example in amounts of from 0 to 100% by weight, preferably from 0 to 60% by weight. The weight data are based on the resulting polymer.

The glass transition temperature ($T_g$) of the monomer mixture A (that is, of a polymer which has been built up from the monomer mixture A) is less than or, at the most, equal to the glass transition temperature of the polymer B.

The $T_g$ of the monomer mixture A is with particular preference at least 10° C., especially 20° C., lower than that of the polymer B.

The $T_g$ of the monomer mixture A is preferably from 0 to 100° C. and with particular preference from 5 to 50° C.

The $T_g$ of the polymer B is preferably from 10 to 150° C. and with particular preference from 40 to 130° C.

In this context, the $T_g$ is calculated in accordance with Fox from the $T_g$ of the homopolymers formed from the monomers (T.G. Fox, Bull. Am. Phys. Soc. Ser II, 1 (1956)123)

$$\frac{1}{T_g} = \frac{X_A}{T_g(A)} + \frac{X_B}{T_g(B)} + \ldots$$

$T_g(A),(B)$: $T_g$ of the homopolymer of monomer (A), (B)

$X_A$, $X_B$: mass fraction of the monomer (A), (B)

The emulsion polymerization can be carried out in a customary manner, for example at from 30 to 95° C. in the presence of a water-soluble initiator.

Examples of suitable initiators are sodium, potassium and ammonium persulfate, tert-butyl hydroperoxides, water-soluble azo compounds, or redox initiators.

In the case of hydrogen peroxide as initiator it is preferred also to use small amounts of Cu(II) or Fe(III) as catalyst.

The aqueous emulsion polymer dispersion obtained after the emulsion polymerization preferably has a solids content of from 10 to 65, preferably from 30 to 60 and, with particular preference, from 40 to 55% by weight.

The emulsion polymer, or the aqueous dispersion, is used as a binder for aqueous cosmetic compositions, especially for aqueous nail varnish compositions.

The novel aqueous cosmetic compositions can comprise further constituents, examples being pigments, dyes, dispersants, wetting agents, thickeners, humectants, leveling agents, preservatives, foam inhibitors, gelling agents, buffers and UV absorbers. The selection of such possible constituents is within the ability of the skilled worker in the cosmetics field.

Any pigments or dyes used should be relatively lightfast and non-bleeding. Substances which impart a pearl luster, such as mica, guanine, bismuth oxychloride or titanium dioxide on mica, can likewise be used. Numerous examples of suitable pigments and dyes are given in Madison G. deNavarre, The Chemistry and Manufacture of Cosmetics, Vol. 4, pp.996–998 (2nd ed.).

Dispersants and wetting agents are frequently used as surface-active agents in these nail coating formulations in order to assist the uniform distribution of the pigment. Inorganic pigments are inherently hydrophilic and can readily be dispersed in an aqueous emulsion system. Organic pigments are hydrophobic and necessitate a dispersant or wetting agent, which reduces the surface tension and allows uniform distribution. A listing of suitable surface-active agents is given in Encyclopedia of Chemical Technology, Surfactants, Vol. 19, p. 584 (1969), and the choice to be made in each case is within the knowledge and ability of the skilled worker.

Thickeners serve to prevent separation and settling. Examples of suitable thickeners are natural gums, such as guar, gum arabic, cellulose and cellulose derivatives, silicates, such as V-gum®, clays, such as stearalkonium hectorite, and synthetic polymers, such as acrylates, for example Carbopol® and Acrysols®.

Examples of humectants are mono- and polyglycols, mono- and polyglycerols, sugar alcohols, alkylene oxides and polyalkylene oxides, especially ethylene and propylene oxides (EO and PO), saccharides, glucosides, amino acids, urea and adducts of EO and/or PO with these compounds. The humectants transmit moisture to the skin and are generally used in amounts of from 0.01 to 30% by weight, preferably from 0.1 to 10% by weight, based on the cosmetic composition.

Leveling agents can be added to reduce the temperature at which the film is able to form. The leveling agents therefore function only during film formation. For the purposes of the invention, these agents must be soluble in water. One group of appropriate leveling agents comprises the glycol ethers, such as ethylene glycol monobutyl ether, diethylene glycol monomethyl ether, propylene glycol monomethyl ether and dipropylene glycol monomethyl ether.

To prevent bacterial and fungal growth during storage of the nail coating formulations it is common to use preservatives. Preservatives suitable for this purpose are those generally used, for example lower alkyl esters of p-hydroxybenzoic acid, such as methyl, ethyl, butyl and hexyl p-hydroxybenzoate, organic salts, such as potassium sorbate, inorganic salts, such as mercury salts, and formaldehyde and formaldehyde donors.

To prevent foaming and the formation of bubbles during preparation and application to the nails it is possible to use foam inhibitors. Examples of suitable foam inhibitors are unsubstituted and substituted organopolysiloxanes, such as methylsilicone and diethylsilicone, silicon dioxide, mixtures of silicon and silicon dioxide, and of organopolysiloxanes and silicon dioxide, and polyoxyethylene-polyoxypropylene condensates.

Gelling agents remove heavy metal ions, which may impair the stability of nail varnishes. Suitable gelling agents are ethylenediaminetetraacetic acid (EDTA) and its mono- and tetrasodium salt, and tetrasodium pyrophosphate.

If necessary, the nail coating formulation is buffered so that the pH is preferably from 7 to 10, more preferably 8.0±0.5.

The purpose of UV absorbers is to prevent the damaging effects of UV rays on the polymer, chalking of the pigment or dye, and embrittlement of the nail coating film. A listing of suitable UV absorbers is given in Encyclopedia of Chemical Technology, Vol. 21, pp.115–122 (1969).

The content of the emulsion polymer in the cosmetic composition is preferably 1–70% by weight, more preferably 20–65% by weight and, with particular preference, 25–50% by weight, based on the overall weight of the cosmetic composition. If the amount used is less than 1%, the effect according to the invention may not be obtained. If, on the other hand, it is greater than 70% the viscosity of the novel composition is too high.

The dispersion of the emulsion polymer contains little coagulum and features fine disperse particles.

The aqueous cosmetic compositions, especially nail varnish compositions, have a high water stability, in other words low water absorption, good film-forming properties, good gloss and, in particular, good adhesion to keratin-containing substrates such as fingernails.

EXAMPLES

A) Preparing the Polymer B) by Solution Polymerization

In a glass flask equipped with reflux condenser, anchor stirrer, 2 dropping funnels and a thermostat-controlled oil-bath the initial charge was heated to 105° C. in a nitrogen atmosphere with stirring. On reaching this temperature, feed stream 2 was started and was metered in over the course of 5 hours. 15 minutes after the start of feed stream 2, feed stream 1 was started and was metered in over the course of 3.5 hours. The polymer solution was then cooled to 90° C. and was neutralized with feed stream 3 over the course of 15 minutes. Subsequently, stirring was continued for 15 minutes more. The polymer solution was then dispersed by incorporating feed stream 4, with stirring, over the course of 1 hour. The compositions and characteristics are indicated in Table 1.

TABLE 1

| Synthesis of the polymers B (shell polymers) (All figures in grams) | | | | |
|---|---|---|---|---|
| # | B1 | B2 | Comp.B1 | Comp.B2 |
| Initial charge: | | | | |
| Isobutanol | 140 | 136 | 170 | 170 |
| Part of feed stream 1 | 144 | 144 | 144 | 144 |
| Feed stream 1: | | | | |
| Acrylic acid | 160 | 160 | 80 | 80 |
| Styrene | 640 | — | — | — |
| n-Butyl methacrylate | — | 640 | — | — |
| n-Butyl acrylate | — | — | 560 | 480 |
| Methyl methacrylate | — | — | 160 | 240 |

TABLE 1-continued

Synthesis of the polymers B (shell polymers)
(All figures in grams)

| # | B1 | B2 | Comp.B1 | Comp.B2 |
|---|---|---|---|---|
| Feed stream 2: | | | | |
| Isobutanol | 240 | 240 | 104 | 104 |
| tert-Butyl peroctoate | 16 | 16 | 16 | 16 |
| Feed stream 3: | | | | |
| Aq. ammonia soln. (25% by wt.) | 151 | 151 | 92 | 76 |
| Feed stream 4: | | | | |
| Water | 1,300 | 1,200 | 1,600 | 1,600 |
| Characteristics of the polymer solution before adding feed streams 3 and 4: | | | | |
| K value | 31.8 | 33.6 | 28 | 29.4 |
| Solids content (%) | 68 | 69 | 75 | 74 |
| Characteristics of the aqueous polymer solution after adding feed streams 3 and 4: | | | | |
| Solids content (%) | 31.6 | 31.7 | 29.0 | 28.1 |
| pH | 8.1 | 7.8 | 8.8 | 7.6 |
| Isobutanol (%) | 14.4 | 14.8 | 10.2 | 9.9 |
| Viscosity (mPas) | pasty | pasty | 8,700 | pasty |

B) Emulsion Polymerization

Procedure:

The initial charge was heated to 85° C. with stirring in a nitrogen atmosphere, during which feed stream 1 was metered in. Then 17 g of feed stream 3 were added. Subsequently, feed stream 2 was metered in over 2 hours and the remainder of feed stream 3 was metered in over 2.5 hours. Subsequently, stirring was continued for 1 hour more at 85° C. and then the mixture was cooled to room temperature.

LT: Clouding of the dispersion or solution with a polymer content of 0.01% by weight relative to water, determined by measuring the light flux. LT is the light transmittance in % (the greater LT, the smaller the polymer particles).

TABLE 2

Synthesis of the emulsion polymers (Amounts in grams)

| # | B3 | B4 | Comp.B3 | Comp.B4 |
|---|---|---|---|---|
| Initial charge: | | | | |
| Aq. polymer solution from Table 1, No. | B1 | B2 | Comp.B1 | Comp.B2 |
| Amount (liquid) | 237.5 | 158 | 258.75 | 532 |
| Amount (solid) | 75 | 50 | 75 | 150 |
| Feed stream 1: | | | | |
| Water | 450 | 500 | 337.5 | 675 |
| Copper vitriol | 0.01 | 0.01 | 0.01 | 0.02 |
| Feed stream 2: | | | | |
| Styrene | 224 | — | 232.5 | 465 |
| n-Butyl methacrylate | — | 450 | — | — |
| n-Butyl acrylate | 201 | — | 192.5 | 385 |
| Methyl methacrylate | — | — | — | — |
| Feed stream 3: | | | | |
| Hydrogen peroxide (12%) | 42 | 41.5 | 42 | 83 |
| Feed stream 4: | | | | |
| Water | — | — | 100 | — |

TABLE 2-continued

Synthesis of the emulsion polymers (Amounts in grams)

| # | B3 | B4 | Comp.B3 | Comp.B4 |
|---|---|---|---|---|
| Characteristics of the aqueous polymer dispersions | | | | |
| Solids content (%) | 43.3 | 42.9 | 42.0 | 45.6 |
| pH | 8.6 | 8.1 | 9.4 | 8.0 |
| LT | 38 | 55 | 54 | 55 |
| Isobutanol (%) | 3.0 | 2.0 | 2.3 | 2.5 |
| Viscosity (mPas) | 100 | 220 | 240 | 270 |

TABLE 3

Test results

| | B3 | B4 | Comp. B3 | Comp. B4 |
|---|---|---|---|---|
| Polymer B) | 20 AA, 80S | 20 AA, 80 BMA | 10 AA, 70 BA, 20 MMA | 10 AA, 60 BA, 30 MMA |
| Monomers A) | 52.7% of S, 47.3% of BA | 100% of n-BMA | 54.7% of S, 45.3% of BA | 54.7% of S, 45.3% of BA |
| $T_g$ of the polymer B) | 111° C. | 47° C. | −11° C. | 0.7° C. |
| $T_g$ of the monomers A) | 17° C. | 32° C. | 20° C. | 20° C. |
| Water absorption (%) | 1.1 | 1.8 | 3.6 | 4.0 |

$T_g$ = glass transition temperature according to Fox

Determining the Water Absorption

Three film sections measuring about 2×2 cm (thickness 0.5–1 mm) are weighed (weight Wa) and then stored in water at room temperature. After 24 hours, the film sections are back-weighed while wet (W24). The water absorption in % is calculated from 100×(W24−Wa)/Wa. The mean of the three values is calculated.

We claim:

1. An aqueous cosmetic composition, comprising an emulsion polymer, wherein the emulsion polymer is obtained by emulsion polymerization of a monomer mixture A in the presence of a polymer B, wherein said monomer mixture A comprises:
a) from 50 to 100% by weight, of the total weight of monomer mixture A, of a monomer selected from the group consisting of $C_1$–$C_{18}$ alkyl (meth)acrylates, vinyl esters, vinylaromatic compounds, and mixtures thereof, wherein said polymer B has been prepared from:
$b_1$) from 5 to 50% by weight, of the total weight of polymer B, of monomers having at least one ionic group or one group which can be converted into an ionic group,
$b_2$) from 0 to 95% by weight, of the total weight of polymer B, of $C_1$–$C_{18}$ alkyl (meth)acrylates, vinyl esters, vinylaromatic compounds or mixtures thereof, and
$b_3$) from 0 to 50% by weight, of the total weight of polymer B, of monomers other than those described in $b_1$, and $b_2$, and wherein the glass transition temperature of the polymer prepared from monomer mixture A is less than or equal to that of polymer B.

2. The aqueous cosmetic composition of claim 1, wherein said polymer B has been prepared from 10 to 30% by weight of monomers $b_1$, from 60 to 90% by weight of monomers $b_2$, and from 0 to 30% by weight of monomers $b_3$.

3. The aqueous cosmetic composition of claim 1, wherein the weight-average molecular weight of said polymer B is from 40,000 to 120,000.

4. The aqueous cosmetic composition of claim 1, wherein said polymer B is prepared by bulk or solution polymerization.

5. The aqueous cosmetic composition of claim 1, wherein the proportion by weight of polymer B is from 5 to 25 parts by weight, of the sum of polymer B and monomer mixture A.

6. The aqueous cosmetic composition of claim 1, wherein the content of the emulsion polymer in said composition is from 25–50% by weight, of the total weight of the cosmetic composition.

7. The aqueous cosmetic composition of claim 1, wherein said monomers having at least one ionic group or one group which can be converted into an ionic group are selected from the group consisting of polymerizable carboxylic acid, unsaturated sulfonic acid, unsaturated phosphoric acid, and unsaturated phosphonic acid.

8. The aqueous cosmetic composition of claim 7, wherein said polymerizable carboxylic acid is selected from the group consisting of acrylic acid, methacrylic acid, maleic acid and its anhydrides and monoesters, fumaric acid and its monoesters, and itaconic acid.

9. The aqueous cosmetic composition of claim 7, wherein said unsaturated sulfonic acid is selected from the group consisting of styrenesulfonic acid, vinylsulfonic acid, 2-acrylamido-2-methylpropanesulfonic acid, and salts thereof.

10. The aqueous cosmetic composition of claim 7, wherein said unsaturated phosphoric acid and said unsaturated phosphonic acid are selected from the group consisting of vinylphosphonic acid and monophosphates of polymerizable alcohols.

11. The aqueous cosmetic composition of claim 10, wherein said monophosphates of polymerizable alcohols are selected from the group consisting of monophosphates of butanediol monoacrylate and monophosphates of hydroxyethyl methacrylate.

12. The aqueous cosmetic composition of claim 1, wherein said monomers having at least one ionic group or one group which can be converted into an ionic group are selected from the group consisting of (meth)acrylic esters of amino alcohols, (meth)acrylamides of amino alcohols, dialkylaminostyrenes, vinylpyridines, and quarternized compounds thereof prepared by quaternization with a quaternizing reagent selected from the group consisting alkyl halides, benzyl halides, and dialkyl sulfates.

13. The aqueous cosmetic composition of claim 12, wherein said (meth)acrylic esters of amino alcohols and (meth)acrylamides of amino alcohols are selected from the group consisting of dialkylaminoalkyl (meth)acrylates and dialkylaminoalkyl(meth)-acrylamides.

14. The aqueous cosmetic composition of claim 12, wherein said (meth)acrylic esters of amino alcohols and (meth)acrylamides of amino alcohols are selected from the group consisting of N,N-dimethylaminoethyl (meth) acrylates, N,N-diethylaminoethyl methacrylate, and N,N-dimethylaminopropylacrylamide.

15. The aqueous cosmetic composition of claim 12, wherein said dialkylaminostyrenes are selected from the group consisting of N,N-dimethylaminostyrene and N,N-dimethylaminomethylstyrene.

16. The aqueous cosmetic composition of claim 12, wherein said vinylpyridines are selected from the group consisting of 4-vinylpyridine and 2-vinylpyridine.

17. The aqueous cosmetic composition of claim 1, wherein said monomers having at least one ionic group or one group which can be converted into an ionic group are selected from the group consisting of N-(3-sulfopropyl)-N-methacryloyloxyethyl-N,N-dimethylammonium betaine and N-carboxymethyl-N-methacryloyloxyethyl-N,N-dimethylammonium betaine.

18. The aqueous cosmetic composition of claim 1, wherein said $C_1$–$C_{18}$ alkyl (meth) acrylates are selected from the group consisting of methyl methacrylate, methyl acrylate, n-butyl acrylate, ethyl acrylate, 2-ethylhexyl acrylate, n-butyl methacrylate, lauryl acrylate, lauryl methacrylate, stearyl acrylate, and stearyl methacrylate.

19. The aqueous cosmetic composition of claim 1, wherein said vinyl esters are selected from the group consisting of vinyl esters of carboxylic acids having 1 to 20 C atoms.

20. The aqueous cosmetic composition of claim 1, wherein said vinyl esters are selected from the group consisting of vinyl laurate, vinyl stearate, vinyl propionate, and vinyl acetate.

21. The aqueous cosmetic composition of claim 1, wherein said vinylaromatic compounds are selected from the group consisting of vinyltoluene, α-methylstyrene, p-methylstyrene, α-butylstyrene, 4-n-butylstyrene, 4-n-decylstyrene, and styrene.

22. The aqueous cosmetic composition of claim 1, wherein said monomers other than those described in $b_1$, and $b_2$ are selected from the group consisting of hydroxyl-containing monomers, amides of ethylenically unsaturated mono- and dicarboxylic acids, nitrites, vinyl halides, and nonaromatic hydrocarbons.

23. The aqueous cosmetic composition of claim 22, wherein said hydroxyl-containing monomer is a hydroxyalkyl (meth)acrylate.

24. The aqueous cosmetic composition of claim 23, wherein said hydroxyalkyl (meth)acrylate is selected from the group consisting of hydroxypropyl (meth)acrylate and hydroxyethyl (meth)acrylate.

25. The aqueous cosmetic composition of claim 22, wherein said amides of ethylenically unsaturated mono- and dicarboxylic acids are selected from the group consisting of acrylamide, methacrylamide, N-methylolacrylamide, N-methylolmethacrylamide, N-methylolacrylamides which are etherified with a $C_1$–$C_6$ monohydric alcohol, and N-methylolmethacrylamides which are etherified with a $C_1$–$C_6$ monohydric alcohol.

26. The aqueous cosmetic composition of claim 22, wherein said nitriles are selected from the group consisting of acrylonitrile and methacrylonitrile.

27. The aqueous cosmetic composition of claim 22, wherein said vinyl halides are selected from the group consisting of vinyl chloride and vinylidene chloride.

28. The aqueous cosmetic composition of claim 22, wherein said nonaromatic hydrocarbons are selected from the group consisting of butadiene, isoprene, chloroprene, ethylene, propylene, and isobutylene.

29. The aqueous cosmetic composition of claim 1, wherein:

said monomers having at least one ionic group or one group which can be converted into an ionic group are selected from the group consisting of acrylic acid, methacrylic acid, maleic acid and its anhydrides and monoesters, fumaric acid and its monoesters, itaconic acid, styrenesulfonic acid, vinylsulfonic acid, 2-acrylamido-2-methylpropanesulfonic acid, vinylphosphonic acid, monophosphates of butanediol monoacrylate, monophosphates of hydroxyethyl methacrylate, N,N-dimethylaminoethyl (meth) acrylates, N,N-diethylaminoethyl methacrylate, and N,N-dimethylaminopropylacrylamide, N,N-dimethylaminostyrene, N,N-dimethylaminomethylstyrene, 4-vinylpyridine, 2-vinylpyridine, N-(3-sulfopropyl)-N-methacryloyloxyethyl-N,N-dimethylammonium betaine, and N-carboxymethyl-N-methacryloyloxyethyl-N,N-dimethylammonium betaine;

said $C_1$–$C_{18}$ alkyl (meth)acrylates are selected from the group consisting of methyl methacrylate, methyl acrylate, n-butyl acrylate, ethyl acrylate, 2-ethylhexyl acrylate, n-butyl methacrylate, lauryl acrylate, lauryl methacrylate, stearyl acrylate, and stearyl methacrylate;

said vinyl esters are selected from the group consisting of vinyl laurate, vinyl stearate, vinyl propionate, and vinyl acetate;

said vinylaromatic compounds are selected from the group consisting of vinyltoluene, α-methylstyrene, p-methylstyrene, α-butylstyrene, 4-n-butylstyrene, 4-n-decylstyrene, and styrene;

said monomers other than those described in $b_1$, and $b_2$ are selected from the group consisting of hydroxypropyl (meth)acrylate, hydroxyethyl (meth)acrylate, acrylamide, methacrylamide, N-methylolacrylamide, N-methylolmethacrylamide, N-methylolacrylamides which are etherified with a $C_1$–$C_6$ monohydric alcohol, N-methylolmethacrylamides which are etherified with a $C_1$–$C_6$ monohydric alcohol, acrylonitrile, methacrylonitrile, vinyl chloride, vinylidene chloride, butadiene, isoprene, chloroprene, ethylene, propylene, and isobutylene.

* * * * *